US00PP13646P2

(12) United States Plant Patent
van Haaster

(10) Patent No.: US PP13,646 P2
(45) Date of Patent: Mar. 11, 2003

(54) DAHLIA PLANT NAMED 'CAROLINA ORANGE'

(76) Inventor: Ans van Haaster, Hyacintenlaan 15, 2182 DE Hillegom (NL)

( * ) Notice: Subject to any disclaimer, the term of this patent is extended or adjusted under 35 U.S.C. 154(b) by 0 days.

(21) Appl. No.: 10/080,606

(22) Filed: Feb. 22, 2002

(51) Int. Cl.[7] ..... A01H 5/00
(52) U.S. Cl. ..... Plt./321

(58) Field of Search ..... Plt./321

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Dahlia plant named 'Carolina Orange', characterized by its upright, uniformly mounded and compact plant habit; freely branching, full and dense plants; short response time; and dark orange-colored ray florets with bright yellow-colored disc florets.

1 Drawing Sheet

BOTANICAL CLASSIFICATION/CULTIVAR DESIGNATION

*Dahlia variabilis* cultivar Carolina Orange.

BACKGROUND OF THE INVENTION

The present Invention relates to a new and distinct cultivar of Dahlia plant, botanically known as *Dahlia variabilis*, commercially referred to as a pot-type Dahlia, and hereinafter referred to by the name 'Carolina Orange'.

The new Dahlia is a naturally-occurring whole plant mutation of the *Dahlia variabilis* cultivar Ruicaro, disclosed in U.S. Plant Pat. No. 11,566. The new Dahlia was discovered and selected in 1997 by the Inventor as a single flowering plant within a population of plants of the cultivar Ruicaro in a controlled environment in Hillegom, The Netherlands. The selection of this plant was based on its dark orange-colored ray florets.

Asexual reproduction of the new Dahlia by vegetative tip cuttings was first conducted in Hillegom, The Netherlands in 1998. Asexual reproduction by cuttings has shown that the unique features of this new Dahlia are stable and reproduced true to type in successive generations.

SUMMARY OF THE INVENTION

The cultivar Carolina Orange has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Carolina Orange'. These characteristics in combination distinguish 'Carolina Orange' as a new and distinct pot-type Dahlia:

1. Upright, uniformly mounded and compact plant habit.

2. Freely branching, full and dense plants.

3. Short response time.

4. Dark orange-colored ray florets with bright yellow-colored disc florets.

Plants of the new Dahlia differ from plants of the cultivar Ruicaro and the cultivar Carolina Burgundy, U.S. Plant Patent application Ser. No. 10/080,599 filed concurrently, primarily in ray floret coloration.

Plants of the new Dahlia can be compared to plants of the cultivar Maryland, disclosed in U.S. Plant Pat. No. 11,602. However, in side-by-side comparisons conducted in De Lier, The Netherlands, plants of the new Dahlia differed from plants of the cultivar Maryland in the following characteristics:

1. Plants of the new Dahlia flower about one to two weeks earlier than plants of the cultivar Maryland.

2. Plants of the new Dahlia had smaller leaves than plants of the cultivar Maryland.

3. Plants of the new Dahlia had smaller inflorescences than plants of the cultivar Maryland.

4. Plants of the new Dahlia and plants of the cultivar Maryland differed in ray floret coloration.

BRIEF DESCRIPTION OF THE PHOTOGRAPH

The accompanying colored photograph illustrates the overall appearance of the new Dahlia showing the colors as true as it is reasonably possible to obtain in colored reproductions of this type. Colors in the photograph may differ from the color values cited in the detailed botanical description which accurately describe the colors of the new Dahlia. The photograph comprises a side perspective view of a typical flowering plant of 'Carolina Orange'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs, and the following observations and measurements were grown and flowered during the autumn in a glass-covered greenhouse in De Lier, The Netherlands. One rooted cutting was planted in a 10.5-cm container and pinched one week after planting. During the production of these plants, the day temperature ranged from 19 to 21° C., night temperatures ranged from 18 to 20° C., and light levels ranged from 10,000 to 15,000 lux. Measurements and numerical values represent averages of typical flowering plants about eight weeks after planting.

Botanical classification: *Dahlia variabilis* cultivar Carolina Orange.

Commercial classification: Pot-type Dahlia.

Parentage: Naturally-occurring whole plant mutation of *Dahlia variabilis* cultivar Ruicaro, disclosed in U.S. Plant Pat. No. 11,566.

Propagation:

*Type.*—Vegetative tip cuttings.

*Time to initiate roots.*—Summer: About 5 days at 22° C. Winter: About 8 days at 20° C.

*Time to produce a rooted young plant.*—Summer: About 12 days at 22° C. Winter: About 16 days at 20° C.

*Root description.*—Fine and fibrous.

*Rooting habit.*—Freely branching; development of tubers has not been observed.

Plant description:

*Appearance.*—Herbaceous pot-type Dahlia. Inverted triangle; stems mostly upright and somewhat outwardly spreading giving a uniformly mounded appearance to the plant; compact. Moderately vigorous.

*Branching habit.*—Freely branching, about six lateral branches develop per plant; dense and full plants.

*Plant height.*—About 20 cm.

*Plant width or area of spread.*—About 19 cm.

*Lateral branches.*—Length: About 17.5 cm. Diameter: About 7.5 mm. Internode length: About 3.5 cm. Strength: Moderately strong, flexible. Texture: Smooth, glabrous. Color: 144A.

*Foliage description.*—Arrangement: Leaves single or compound with three or five leaflets; opposite. Terminal leaflet length: About 6.75 cm. Terminal leaflet width: About 4.5 cm. Shape: Ovate. Apex: Acute. Base: Attenuate. Margin: Dentate. Texture, upper and lower surfaces: Slightly pubescent. Venation pattern: Pinnate. Color: Young foliage upper surface: 137C. Young foliage lower surface: 138B. Mature foliage upper surface: 137A. Mature foliage lower surface: 138B. Venation, upper surface: 146D. Venation, lower surface: 137C. Petiole: Length: About 3.5 cm. Diameter: About 3 mm. Color, upper and lower surfaces: 147C.

Inflorescence description:

*Appearance.*—Terminal and axillary inflorescences held above the foliage on strong flexible peduncles. Composite inflorescence form with elongated oblong-shaped ray florets and disc florets massed at the center; ray and disc florets arranged acropetally on a capitulum. Inflorescences not fragrant. Inflorescences persistent.

*Flowering response.*—Plants flower continuous and freely from the late spring through the fall.

*Response time* (*time to flowering*).—Short response time; plants begin flowering about six to seven weeks after planting rooted cuttings.

*Postproduction longevity.*—Inflorescences maintain good color and substance for about one to two weeks.

*Quantity of inflorescences.*—At full flower, about 20 open inflorescences and buds per plant.

*Inflorescence bud* (*before showing color*).—Shape: Globular, roughly spherical. Length: About 1 cm. Diameter: About 8 mm. Color: 144B.

*Inflorescence size.*—Diameter: About 7 cm. Depth (height): About 2 cm. Disc diameter: About 1 cm. Receptacle diameter: About 2 cm. Receptacle height: About 5 mm.

*Ray florets.*—Shape: Elongated oblong. Orientation: Initially upright, outer florets perpendicular to peduncle. Aspect: Straight, concave. Length: About 3.5 cm. Width: About 1.5 cm. Apex: Acute. Base: Cuneate; short corolla tube. Margin: Entire. Texture, upper and lower surfaces: Smooth, glabrous. Number of ray florets per inflorescence: About 75 in about six or seven rows. Color: When opening and fully opened, upper surface: 33A; with subsequent development fading to 31A to 31B. When opening and fully, lower surface: 33B.

*Disc florets.*—Shape: Tubular, elongated. Apex: Rounded. Length: About 1 cm. Width: Apex: About 2 mm. Base: About 1 mm. Number of disc florets per inflorescence: About 27. Color: Immature: 15B. Mature: Apex: 9A. Mid-section: 17A. Base: 145C.

*Phyllaries* (*involucral bracts*).—Quantity: About six or seven per inflorescence. Length: About 1.25 cm. Width: About 6 mm. Shape: Narrowly deltoid. Apex: Acute. Base: Cuneate. Margin: Entire. Texture, upper and lower surfaces: Smooth. Color: Upper surface: 137B. Lower surface: 143C.

*Peduncles.*—Length, terminal inflorescence: About 5 cm. Diameter: About 3 mm. Aspect: Erect. Strength: Moderately strong, flexible. Texture: Smooth, glabrous. Color: 146A.

*Reproductive organs.*—Androecium: Present on disc florets only. Stamen quantity: Five per floret. Anther length: About 2 mm. Anther shape: Ovoid. Anther color: 9A. Pollen amount: Moderate. Pollen color: 17A. Gynoecium: Present on both ray and disc florets. Pistil quantity: One per floret. Pistil length: About 9 mm. Stigma color: 14A. Style length: About 8 mm. Style color: 7B. Ovary color: 1C.

*Seed/fruit production.*—Seed nor fruit production has not been observed.

Disease/pest resistance: Resistance to pathogens or pests common to Dahlias has not been observed on plants grown under commercial greenhouse or outdoor conditions.

Weather tolerance: Plants of the new Dahlia have been observed to be wind and rain-tolerant. Plants of the new Dahlia tolerant temperatures from 1° to about 40° C.

It is claimed:

1. A new and distinct cultivar of Dahlia plant named 'Carolina Orange', as illustrated and described.

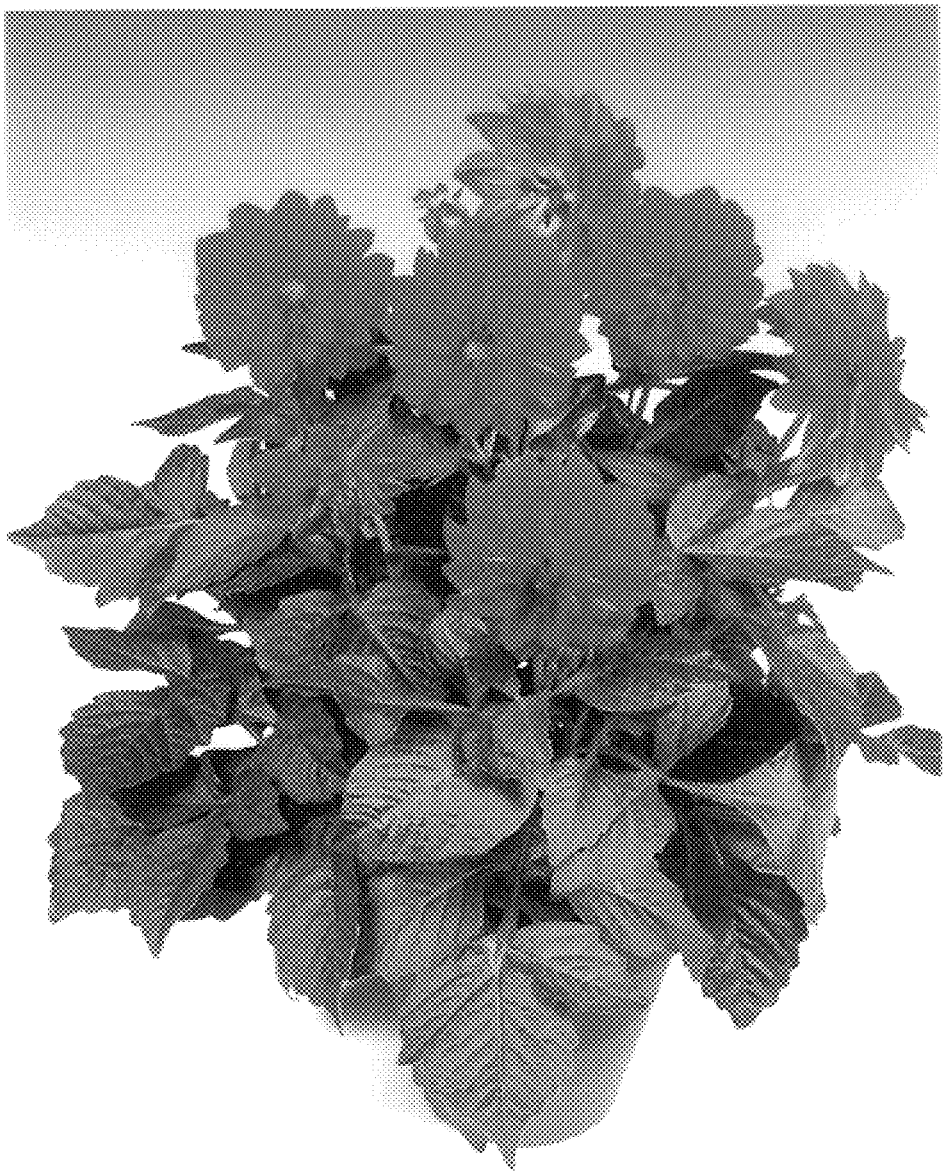

* * * * *